(12) United States Patent
Voigt et al.

(10) Patent No.: US 10,092,368 B2
(45) Date of Patent: Oct. 9, 2018

(54) MEDICAL APPARATUS WITH A MEDICAL OPTICAL APPLIANCE AND A HOLDING DEVICE AND METHOD FOR OPERATING THE MEDICAL APPARATUS

(71) Applicant: Carl Zeiss Meditec AG, Jena (DE)

(72) Inventors: Christian Voigt, Abtsgmuend (DE); Dominik Litsch, Schorndorf (DE); Christine Hanel, Oberkochen (DE)

(73) Assignee: CARL ZEISS MEDITEC AG, Jena (DE)

( * ) Notice: Subject to any disclaimer, the term of this patent is extended or adjusted under 35 U.S.C. 154(b) by 117 days.

(21) Appl. No.: 15/373,797

(22) Filed: Dec. 9, 2016

(65) Prior Publication Data

US 2017/0165026 A1    Jun. 15, 2017

(30) Foreign Application Priority Data

Dec. 15, 2015  (DE) .......................... 10 2015 225 183

(51) Int. Cl.
*A61B 90/25* (2016.01)
*F16M 11/06* (2006.01)
*F16M 11/20* (2006.01)
*A61B 90/50* (2016.01)
(Continued)

(52) U.S. Cl.
CPC ............. *A61B 90/25* (2016.02); *A61B 90/50* (2016.02); *F16M 11/06* (2013.01); *F16M 11/2021* (2013.01); *A61B 2034/2059* (2016.02); *A61B 2090/064* (2016.02); *A61B 2090/504* (2016.02); *A61B 2090/506* (2016.02); *A61B 2090/508* (2016.02); *F16M 2200/044* (2013.01); *F16M 2200/063* (2013.01)

(58) Field of Classification Search
CPC ....................................................... A61B 90/25
USPC .................................................. 318/560, 34
See application file for complete search history.

(56) References Cited

U.S. PATENT DOCUMENTS 7,109,678 B2    12/2006  Kraus et al.
8,744,625 B2 *   6/2014  Negishi .................... B25J 9/161
                                                          345/156
(Continued)

FOREIGN PATENT DOCUMENTS

DE    102004063606    7/2006
DE    102010033326    2/2012
(Continued)

OTHER PUBLICATIONS

German Office Action dated Aug. 18, 2016.

*Primary Examiner* — David S Luo
(74) *Attorney, Agent, or Firm* — Nixon Peabody LLP; Jeffrey L. Costellia (57) ABSTRACT

The invention relates to a medical apparatus having a medical optical appliance and a holding device with at least two holding arms which are connected movably to one another with at least one degree of freedom of movement via a joint and with an actuator which is connected to the two holding arms in such a way that a force can be exerted via the actuator between the two holding arms in the direction of the degree of freedom of movement. A control unit comprises a first regulator for outputting a first control signal to the actuator via an adjusting element. The medical optical appliance is mounted on the holding device.

9 Claims, 5 Drawing Sheets

(51) Int. Cl.
 *A61B 90/00* (2016.01)
 *A61B 34/20* (2016.01)

(56) References Cited

U.S. PATENT DOCUMENTS

2013/0325032 A1   12/2013   Schena et al.
2015/0351857 A1   12/2015   Vander Poorten et al.

FOREIGN PATENT DOCUMENTS

DE   102011003589   8/2012
DE   102014116103   5/2016

\* cited by examiner

MEDICAL APPARATUS WITH A MEDICAL OPTICAL APPLIANCE AND A HOLDING DEVICE AND METHOD FOR OPERATING THE MEDICAL APPARATUS

CROSS-REFERENCE TO RELATED APPLICATIONS

This application claims priority from and the benefit of German Application No. 10 2015 225 183.7, which is hereby incorporated by reference in its entirety.

TECHNICAL FIELD

The invention relates to a medical apparatus that has a medical optical appliance and a holding device. The holding device comprises at least two holding arms, which are connected movably to one another with at least one degree of freedom of movement via a joint. Moreover, the holding device has an actuator which is connected to the two holding arms in such a way that a force can be exerted via the actuator between the two holding arms in the direction of the degree of freedom of movement. The medical optical appliance is mounted on the holding device. A control unit comprises a first regulator for outputting a first control signal to the actuator via an adjusting element.

BACKGROUND

In many medical procedures, medical optical appliances are used to examine or treat a patient. These appliances are often mounted on an articulated holding device, such that they can be positioned at different positions in the work space and, if appropriate, can be oriented there in a desired direction. In operation, it is often necessary to vary the position and optionally the orientation of the medical optical appliance, for example in order to modify a viewing angle of the operating site by a surgical microscope or to modify a beam direction of a treatment laser. There is therefore a frequent alternation between stationary phases, in which the medical optical appliance is held in a defined position in space, and movement phases, in which the medical optical appliance is transferred from one position to another position.

In a movement phase, the medical optical appliance is intended to be able to be transferred as smoothly as possible by a user, that is to say by application of minimal physical force, from a starting position to an end position. It is known from the prior art to provide the holding device with actuators on the joints, which actuators assist or indeed actually permit a movement of the stand.

DE 10 2004 063 606 A1 discloses a medical apparatus comprising a medical optical appliance in the form of a surgical microscope which is mounted on a holding device. For force-free movement of the surgical microscope, the medical apparatus has electric motors on the joints of the holding device. Angle settings in the rotary joints are detected by position sensors. Current control curves are stored in an electronic memory, and current values can be determined from these as a function of the detected angle settings. A current value is determined from the detected angle settings with the aid of the current control curves, with which current value the electric motors are powered such that a defined torque is generated in the electric motors. In this way, a static load torque can be compensated by the counter-torque generated in the electric motors, such that the surgical microscope can be moved by a user without any apparent force. However, the medical apparatus according to DE 10 2004 063 606 A1 has disadvantages in the unguided state when a user is not actively moving the medical apparatus or holding it at a position in space. In this case, drift can occur, i.e. a creeping movement of the medical optical appliance away from a set position. A further disadvantage of the medical apparatus is that (inadvertent) bumping against the holding device or the surgical microscope can result in an uncontrolled movement, which is something to be avoided in a surgical situation.

To avoid uncontrolled movements, it is known from the prior art to provide holding devices with brakes that can be activated by a user in order to suppress some or all of the degrees of freedom of movement of the holding device, such that a position and/or orientation of the medical optical appliance in space is maintained. Holding devices with brakes are disclosed, for example, in the documents DE 101 44 033 A1, DE 202 18 693 U1 and DE 20 2007 003 822 U1. However, a disadvantage of using brakes is that they increase the complexity of the overall system, have a flexibility that promotes a tendency toward vibration, and generally have to be actively opened and closed a number of times during an operation, which impedes the progress of the operation

BRIEF DESCRIPTION

An object of the present invention is to develop a medical apparatus with a medical optical appliance and a movement-controlled holding device such that a secure stationary state is ensured. A further object is to make available a suitable operating method for a medical apparatus of this kind.

The objects are achieved by a medical apparatus having the features of claim 1 and by a method having the features of claim 6.

According to the invention, the control unit of the medical apparatus comprises means for measuring a kinematic state on the joint and a second regulator for outputting a second control signal to the actuator via the adjusting element. The control unit is configured in such a way that it can be set to a first operating state and to a second operating state, wherein, in the first operating state, the actuator is controlled in a position-regulated manner via the first regulator and the adjusting element as a function of the kinematic state measured on the joint, in such a way that a relative position between the two holding arms is maintained at least substantially independently of external or internal influences on the holding device or the medical optical appliance, and wherein, in the second operating state, the actuator is controlled in a force-regulated manner via the second regulator and the adjusting element, in such a way that a relative movement between the two holding arms is permitted.

In the context of the present invention, the term "force" is to be understood as meaning both a directed longitudinal force and also a torque acting about a rotation axis. Analogously, the terms "force regulation" and "force-regulated" are not limited to regulations of directed longitudinal forces but also include regulations of torques.

Within the meaning of the present invention, a "measurement of a kinematic state" is to be understood as a measurement of one or more kinematic variables. In particular, this includes measurements of rotation angles or translatory excursions, angle velocities or translatory velocities and angle accelerations or translatory accelerations or combinations of said variables. The means for measuring a kinematic state are configured to determine a kinematic state on the joint, for example by direct measurement of one or more kinematic variables on the joint or indirectly through a device for tracking the position of the medical optical appliance in space and by back-calculation to kinematic variables on the joint.

During an operation of the medical apparatus in which the control unit is set to the second operating state, the actuator is controlled under force regulation. In this way, a relative movement between the two holding arms is permitted by exerting an external force on the holding device or the medical optical appliance. Depending on the configuration of the regulation, the external force can also be very small, such that a user is able to move the medical optical appliance almost without any force. After a change to the first operating state of the control unit, the actuator is controlled under position regulation. The change preferably takes place when the medical optical appliance is intended to be held at a defined location in space, for example at the location where it is situated when the change of the operating states is initiated. The position regulation ensures that the medical optical appliance remains at the set location, in particular also when external or internal forces influence the medical optical appliance or the holding device. A further advantage in a medical apparatus according to the invention is that it is possible to dispense with the use of brakes for holding the medical optical appliance at a desired position in the work space, or that existing brakes, which may be present for safety reasons for example, can have smaller dimensions.

In one embodiment of the invention, the control unit is configured such that, in the second operating state, it controls the actuator via the second regulator as a function of a kinematic state measured on the joint. In this way, it is possible in particular for the same sensors used in the first operating state of the control unit during the position-regulated control of the actuator for measuring a kinematic state to be used to measure a possibly different kinematic state in the second operating state of the control unit during a force-regulated or force-controlled control of the actuator. In this way, a small number of sensors suffices for the operation of the medical apparatus with the control unit in the first operating state and in the second operating state.

In a further embodiment of the invention, the control unit comprises means for determining a force generated by the actuator, and the control unit is configured in such a way that, in the second operating state, the actuator is controlled via the second regulator as a function of the measured force. In this way, for the second operating state, a force regulator can be obtained that is distinguished by particularly precise adjustment of the force.

In a further embodiment of the invention, the medical apparatus comprises an enabling unit which can be activated by a user and which is configured in such a way that an activation of the enabling unit causes a change of the control unit from the first operating state to the second operating state or vice versa. With the aid of the enabling unit, the medical apparatus can thus be set by a user, when so required, to a state in which a movement of the medical optical appliance is permitted by application of a defined force (second operating state of the control unit) or in which the medical optical appliance is held securely in a defined position and/or orientation in space (first operating state of the control unit).

In a further embodiment of the invention, the medical apparatus has means for blocking a relative movement between the two holding arms, and the control unit is configured to cause the relative movement to be blocked when a limit value for the force generated by the actuator is exceeded. The activation of the means for blocking the relative movement constitutes a safety mechanism which, for example, can reduce the danger of overloading of the actuators, of the holding arms or of other parts of the medical apparatus caused by the influence of unusually strong external forces, wrong operation or control errors. Alternatively or in addition, limit values for kinematic state variables of individual, several or all of the holding arms of the holding device or for the medical optical appliance can also be defined in a suitable, for example spatially fixed, coordinates system in the control unit. The limit values can also be configured such that critical settings of the holding device in the work space are avoided, for example in order to ensure a minimum distance of the medial optical appliance from a patient.

A method according to the invention for operating a medical apparatus comprises the method steps of:
 bringing the control unit to the first operating state, in which a kinematic state on the joint is measured and in which, via the first regulator and the adjusting element, the actuator is controlled in a position-regulated manner as a function of the measured kinematic state, such that a relative position between the two holding arms is at least substantially maintained; and
 changing the operating state of the control unit to the second operating state, in which the actuator is controlled in a force-regulated manner via the second regulator and the adjusting element, such that a relative movement between the two holding arms is permitted.

Alternatively or in addition, the method according to the invention can also be carried out in the reverse sequence, i.e. starting by setting the control unit to the second operating state and subsequently changing the operating state of the control unit to the first operating state. Furthermore, multiple changes between the operating states of the control unit are also possible. Without departing from the scope of the invention, the control unit, between a change from the first operating state to the second operating state or vice versa, can also adopt further operating states, in which the medical optical appliance is guided on the holding device by the user, for example without regulation, or is moved in a defined manner from one position to another position in the work space with the aid of the actuator or of several actuators on several joints. An enabling unit would in this case preferably be configured such that the different operating states can be selected by a user.

The method according to the invention is distinguished by the fact that the medical optical appliance, on the one hand in the force-regulated operating state of the control unit, can be brought from one position to another by application of a defined force by a user or even in a manner almost free of force, and, on the other hand in the position-regulated operating state, a secure positioning of the medical optical appliance in the work space is ensured also under the influence of external or internal forces on the appliance or the holding device.

In one embodiment of the method, the change between the operating states is initiated by activation of an enabling unit. Without departing from the scope of the invention, in this case a change from the first operating state to the second operating state, or vice versa, can be initiated once or several times in succession.

In a further embodiment of the method, the first regulator and the second regulator are adapted to each other such that, without the influence of external forces in the second operating state directly after the change, a force exerted by the actuator differs by less than 10%, preferably by less than 5%, more preferably by less than 1%, from a force exerted by the actuator in the first operating state directly before the change. In this way, it is possible to reduce or avoid a jump in the force exerted by the actuator or in the moment at a transition between the operating states. This aspect is particularly important at a transition from the position-regulated operating state to the force-regulated operating state, in order to avoid a sudden movement of the medical optical appliance (for example a sinking movement caused by gravity).

In a further embodiment of the method, a force generated by the actuator is measured, and, if a limit value is exceeded, means for blocking a relative movement between the two holding arms are activated, by which means the relative movement is braked and/or suppressed. A safety mechanism is thereby provided which, for example, can avoid the danger of overloading of the medical apparatus.

BRIEF DESCRIPTION OF THE DRAWINGS

The invention is described in more detail below with reference to figures. In the drawings.

The present disclosure is susceptible of various modifications and alternative forms, and some representative embodiments have been shown by way of example in the drawings and will be described in detail herein. It should be understood, however, that the inventive aspects are not limited to the particular forms illustrated in the drawings. Rather, the disclosure is to cover all modifications, equivalents, and alternatives falling within the spirit and scope of the disclosure as defined by the appended claims.

DETAILED DESCRIPTION OF ILLUSTRATED EXAMPLES

Figure 1:
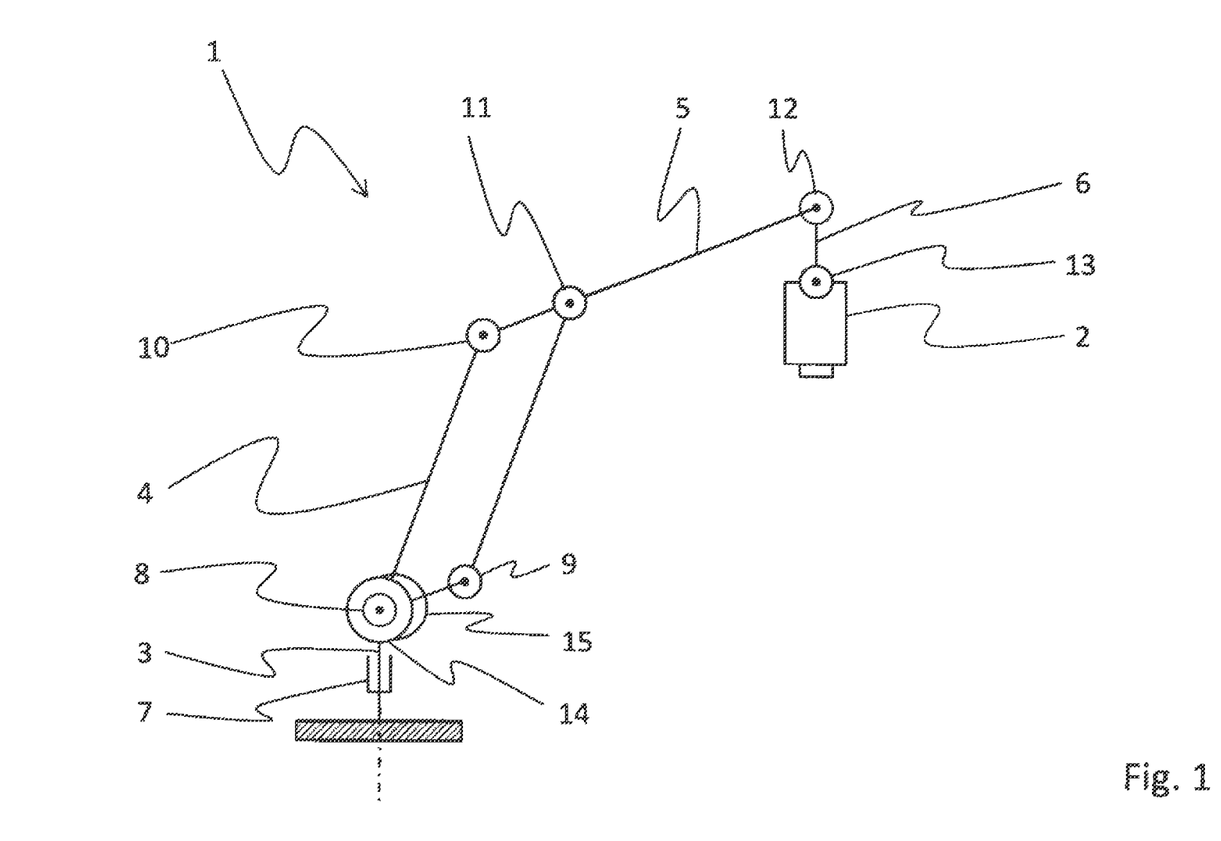
FIG. 1 shows a first embodiment of a medical apparatus according to the invention.

A first illustrative embodiment of a medical apparatus according to the invention is shown in FIG. 1. The medical apparatus has a medical optical appliance in the form of a surgical microscope 2, which is mounted on a holding device in the form of a stand 1.

During an operation, it is often necessary to vary the position of the surgical microscope in space. Depending on the particular application, these variations can entail changes in the position and also changes in the angular orientation of the surgical microscope in space or combinations of said changes. To be able to achieve this, the stand 1 comprises several holding arms 3, 4, 5, 6, which are connected to one another via joint connections 8, 9, 10, 11, 12.

The stand has a vertically arranged first holding arm 3, which is connected to the floor via a first rotary joint 7 that has a vertically arranged rotation axis. As an alternative to this, the first holding arm 3 can also be secured on a floor plate, which can be equipped with rollers, so as to be able to transport the medical apparatus in the operating theater. By way of the first rotary joint 7, the stand as a whole, with the surgical microscope 2 secured thereon, can be pivoted about the vertical rotation axis. The first holding arm 3 is connected via a second rotary joint 8, which has a horizontally arranged rotation axis, to a second holding arm 4 which, in this illustrative embodiment, is designed as a parallelogram structure. The parallelogram structure comprises a third rotary joint 9, a fourth rotary joint 10 and a fifth rotary joint 11, of which the rotation axes are arranged parallel to the rotation axis of the second rotary joint 8. The upper arm of the parallelogram structure is designed as a third holding arm 5 and extends beyond the fifth rotary joint 11. A front connector rod 6 is arranged at the other end of the third holding arm 5 via a sixth joint 12, on which front connector rod 6 the surgical microscope 2 is in turn mounted via a seventh joint 13. The fifth joint 12 and the sixth joint 13 can be configured with several degrees of freedom of movement, for example with several rotation axes and/or several degrees of freedom of translatory movement.

On one, several or all of the joints of the stand 1, actuators are provided with which a movement of the stand can be assisted or carried out. In this illustrative embodiment, the actuators are explained using the example of a first actuator 14 and of a second actuator 15. The first actuator 14 is arranged between the first holding arm 3 and the second holding arm 4, such that an activation of the first actuator 14 causes a rotation of the second holding arm 4, and of the further stand elements arranged thereon, as a whole, about the rotation axis 8. The second actuator 15 is arranged inside the parallelogram structure of the second holding arm 4, such that an activation of the second actuator causes a displacement inside the parallelogram structure, by which the third holding arm 5 is tilted about the fifth joint 11. Without restricting the generality of the invention, further actuators can alternatively or additionally be provided on other joints of the stand.

The structure of a rotary joint connection for a medical apparatus according to the invention is explained in more detail below on the basis of the connection, shown in FIG. 2, between the first holding arm 3 and the second holding arm 4. The first actuator 14, which is designed as an electric motor in this illustrative embodiment, is arranged between the holding arms 3, 4. The electric motor 14 comprises a stator 20, which is supported on the first holding arm 3, and also a rotor 19 with a shaft 16, which is attached to the second holding arm 4. By means of the electric motor 16, a torque can be generated between the first holding arm 3 and the second holding arm 4.

The shaft 16 is supported on the first holding arm 3 via a first bearing unit 17 and a second bearing unit 18. Shaft 16, first bearing unit 17 and second bearing unit 18 together form the first rotary joint 8 between the two holding arms. The second holding arm 4 is rotatable relative to the first holding arm 3 about the longitudinal axis of the shaft 16, such that the first rotary joint 8 has a degree of freedom of rotary movement.

The medical apparatus furthermore comprises a control unit, which comprises means for measuring a kinematic state in the form of an angle sensor 21, a first regulator 22, a second regulator 23 and an adjusting element 24.

The angle sensor 21 is arranged between the first holding arm 3 and the shaft 16 and is thus suitable for measuring an angle between the first holding arm 3 and the second holding arm 4. The measured angle can be supplied via a signal line 25 to the first regulator 22 and/or to the second regulator 23.

Optionally, the control unit can comprise means for determining a force generated by the first actuator 14 or for determining a torque generated by the first actuator 14, which means are configured as a torque sensor 28 in this illustrative embodiment. The output signal of the torque sensor 28 can be supplied to the first regulator 22 and/or to the second regulator 23 via a third signal line 29, such that it can be used as an input variable for the control algorithms of the first regulator 22 and/or of the second regulator 23.

The first regulator 22 is configured as a position regulator. In this context, the terms "position regulator" or "position-regulated" signify that the regulator is configured to generate an output signal by comparing one or more measured kinematic variables, or variables derived therefrom, with a setpoint value by using a control algorithm known from the prior art, which output signal is converted in the adjusting element to a manipulated variable for the actuator (generally a current), such that the actuator at least substantially maintains a defined position or executes a defined movement, specifically also under the influence of external or internal forces.

The first regulator 22 preferably comprises a control algorithm for active vibration damping. More preferably, the control algorithm of the first regulator comprises adjustable parameters, with which a damping and/or stiffness in the regulated system is adjustable. In a supplementary illustrative embodiment, the medical apparatus comprises a tracking system for determining and monitoring a kinematic state of the medical optical appliance and/or of the holding device in space. The determined kinematic state is supplied via a control line to the control unit and serves as a further input variable for the control algorithms of the first regulator 22 and/or of the second regulator 23. The use of a further input variable permits the use of control algorithms with improved control precision and/or speed.

The second regulator 23 contains a force regulator. In this context, the terms "force regulator" or "force-regulated" signify that the regulator is configured to generate an output signal by comparing one or more measured forces or torques, or variables derived therefrom, with a setpoint value by using a control algorithm known from the prior art, which output signal is converted in the adjusting element to a manipulated variable for the actuator (generally a current), such that the actuator exerts a defined force or a defined torque on the structural elements between which it is arranged. Alternatively, the output signal can also be derived from stored control curves as a function of a measured kinematic state (for example translatory or rotatory position, speed and/or acceleration), similarly to what is disclosed in DE 10 2004 063 606.

The regulators 22, 23 can be constructed in a manner known per se as classical linear regulators, for example as PID regulators, or as state regulators, fuzzy regulators, adaptive regulators, self-learning regulators or in some other way with a central, decentralized or cascaded regulator architecture.

In the present illustrative embodiment, the first regulator 22 and the second regulator 23 are connected via a further signal line 26 to an enabling unit 27, by way of which a user, as will be explained in more detail below, can alternatively enable or suppress a relative movement between the first holding arm 3 and the second holding arm 4. The enabling unit can be configured, for example, as a manual switch, a mouth-operated switch, a foot-operated switch, a touch screen, or a voice-controlled or a gesture-controlled system The adjusting element 24 comprises power electronics, with the aid of which the output signals of the first regulator 22 are converted to a first manipulated variable and the output signals of the second regulator 23 are converted to a second manipulated variable, in this illustrative embodiment in each case currents, for the first actuator 14. The manipulated variables are supplied to the first actuator 14 via a current line 29. Without restricting the generality of the invention, the adjusting element 24 can also comprise different power electronics for the first regulator 22 and the second regulator 23.

Figure 3:
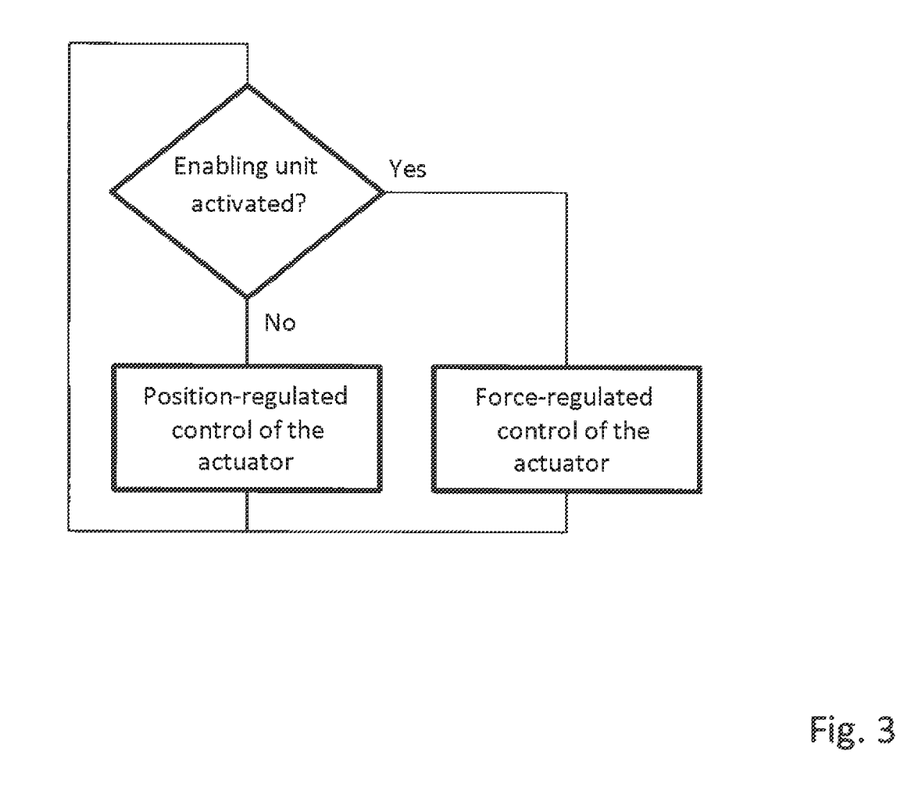
FIG. 3 shows a first illustrative embodiment of a method according to the invention.

A method for operating the medical apparatus is described below with reference to FIG. 3. During operation, a check is continuously made to ascertain whether the enabling unit 27 has been activated by a user. If the enabling unit 27 has been activated, the second regulator 23 is used for the force-regulated control of the actuator. In this operating mode, the surgical microscope 2 can be moved in space by a user applying a defined force. The second regulator 23 can be configured in such a way that loading moments in the stationary state are compensated, in some, several or all positions of the holding device 1 in the work space, at least more or less completely by the actuator 14, 15 or the actuators of the holding device. In this way, the surgical microscope 2 can be moved by a user from one position to another position in the work space almost free of force. The work space is to be understood here as the sum of the positions that the surgical microscope 2 can adopt, taking into account the kinematic constraints predefined by the holding device 1.

By contrast, when the enabling unit 27 is deactivated, the first regulator 22 is used for the position-regulated control of the actuator 14, 15. In this operating mode, the surgical microscope 2 is held by the actuator 14, 15 at least almost constantly at a position and/or in an orientation in the work space, specifically also under the influence of an external or internal force. During operation, external or internal forces may be caused, for example, by a user (inadvertently) bumping against the appliance or leaning on the appliance, or by transmission of ground vibrations or by vibrations of attached auxiliary devices (pumps, fans or the like).

The first regulator 22 and the second regulator 23 are particularly preferably adapted to each other in such a way that a force or a moment generated by the first actuator 14 is maintained at least almost at the same level during a change between the two regulators. In other words, a force generated by the first actuator 14 directly before the change, as a result of the control with one of the two regulators, should differ by less than 10%, preferably by less than 5%, more preferably by less than 1%, from the force generated by the first actuator 14 directly after the change, as a result of the control with the other regulator. This ensures that there is no unwanted sudden movement of the holding device 1, and of the surgical microscope 2 arranged thereon, during a change.

Figure 4:
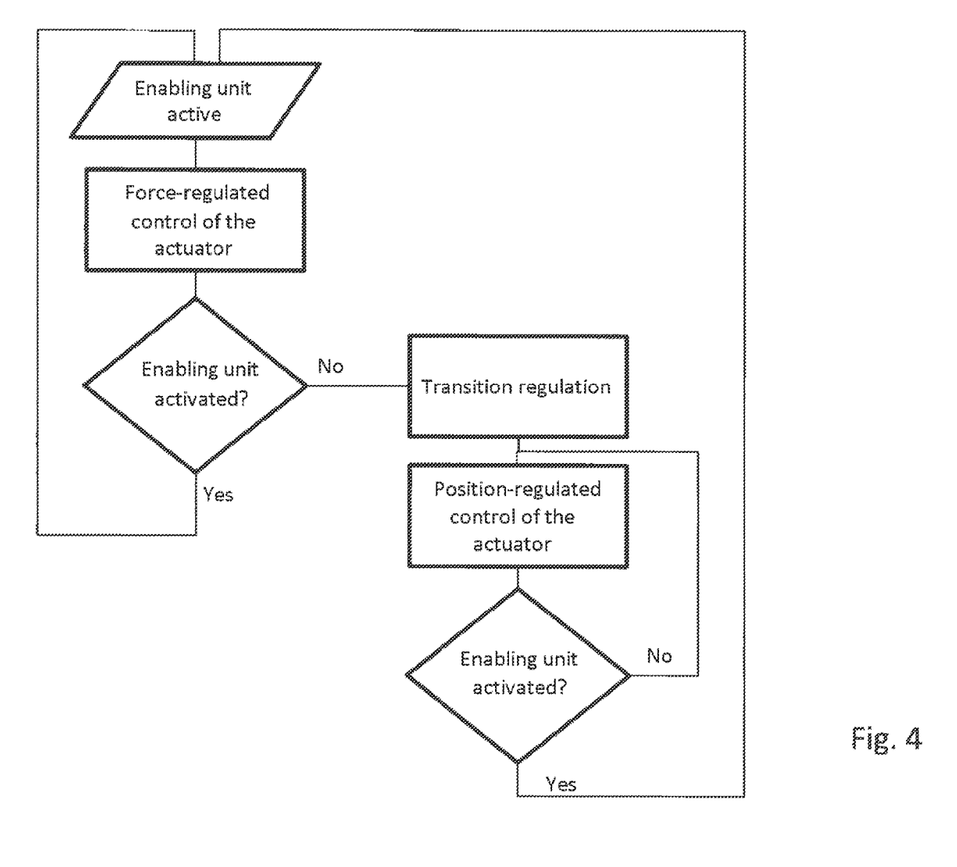
FIG. 4 shows a second illustrative embodiment of a method according to the invention.

FIG. 4 shows a variation of the method for operating the medical apparatus. The method differs from that of FIG. 3 mainly in that a transition regulation is activated during a change from a force regulation to a position regulation. The transition regulation is particularly important when the enabling unit 27 is deactivated during a movement of the surgical microscope 2, that is to say when, during the movement, the second regulator 23 is deactivated and the first regulator 22 is activated and a switch is thus made from force regulation to position regulation. In this case, the transition regulation regulates the braking of the holding device 1 until the stationary state is reached. In one illustrative embodiment, the transition regulation is configured for this purpose such that the holding device 1, with the surgical microscope 2 mounted thereon, comes to a stationary state as quickly as possible without overshooting. Although this has the consequence that the system does not come to a standstill at the position at which the enabling unit 27 was deactivated, there are no vibrations, or virtually no vibrations, during the braking process. In an alternative or supplementary illustrative embodiment, the transition regulation is configured such that the holding device 1 and/or the surgical microscope 2 are brought to the position in which they were located upon the deactivation of the enabling unit 27. An overshooting of the position is accepted in this illustrative embodiment. After the change to position regulation, the enabling unit 27 is then continuously monitored and, in the event of renewed activation, switched back again to force-regulated control of the first actuator 14.

Figure 5:
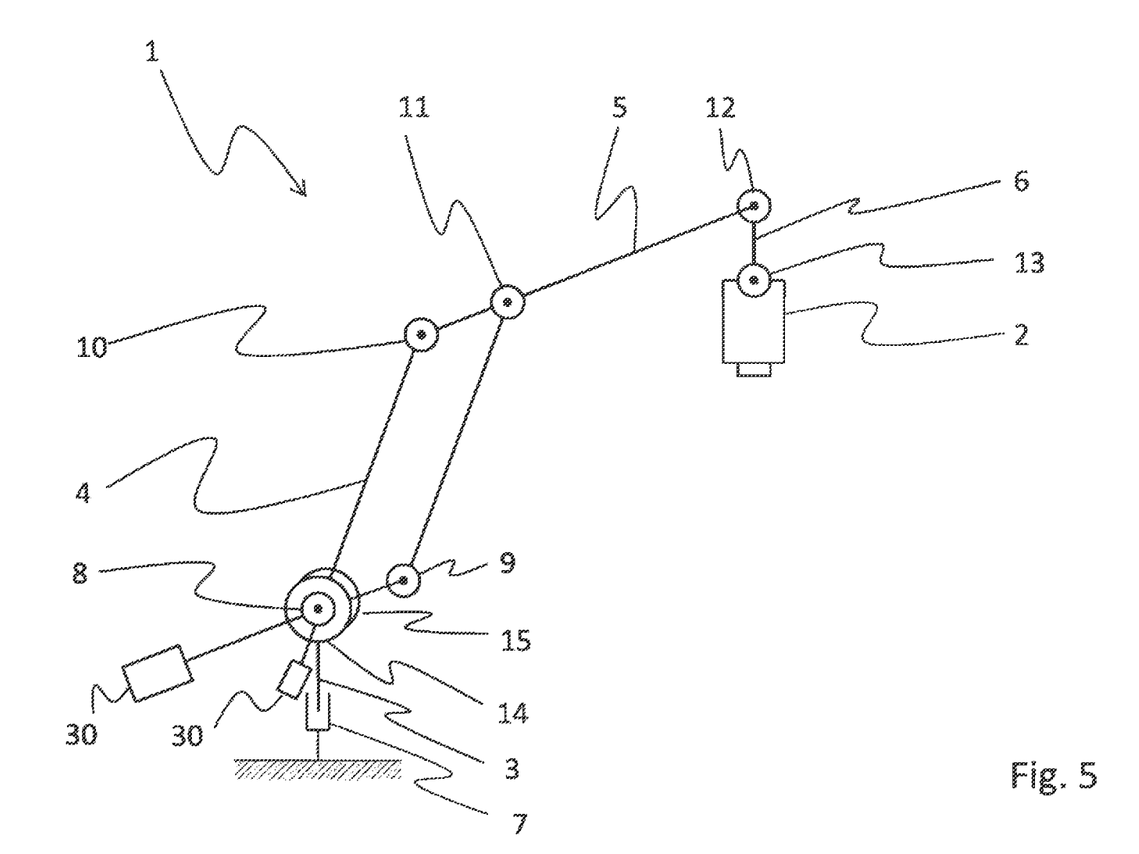
FIG. 5 shows a second embodiment of a medical apparatus according to the invention.

A further illustrative embodiment of a medical apparatus according to the invention is shown in FIG. 5. Components having the same action are provided with the same reference signs as in FIG. 1. The illustrative embodiment according to FIG. 5 differs from the illustrative embodiment according to FIG. 1 in that means are provided for compensation of a static load torque on the holding device 1, which means are configured as counterweights 30 in this illustrative embodiment. With the counterweights, it is possible to compensate for some or all of the static load torques that arise, such that a balance of the holding device in the stationary state is assisted. In this way, the first actuator 14 and the second actuator 15 are unloaded, since at most only some of the required torques for retaining the holding device in a position of equilibrium have to be applied by the actuators. The actuators 14, 15 can thus have smaller dimensions.

In an alternative or supplementary illustrative embodiment, the means for compensation of a static load torque can also comprise force elements, for example springs, pneumatic devices or further actuators, with which forces or moments can be exerted between the holding arms such that a state of equilibrium of the medical apparatus is assisted.

Figure 2:
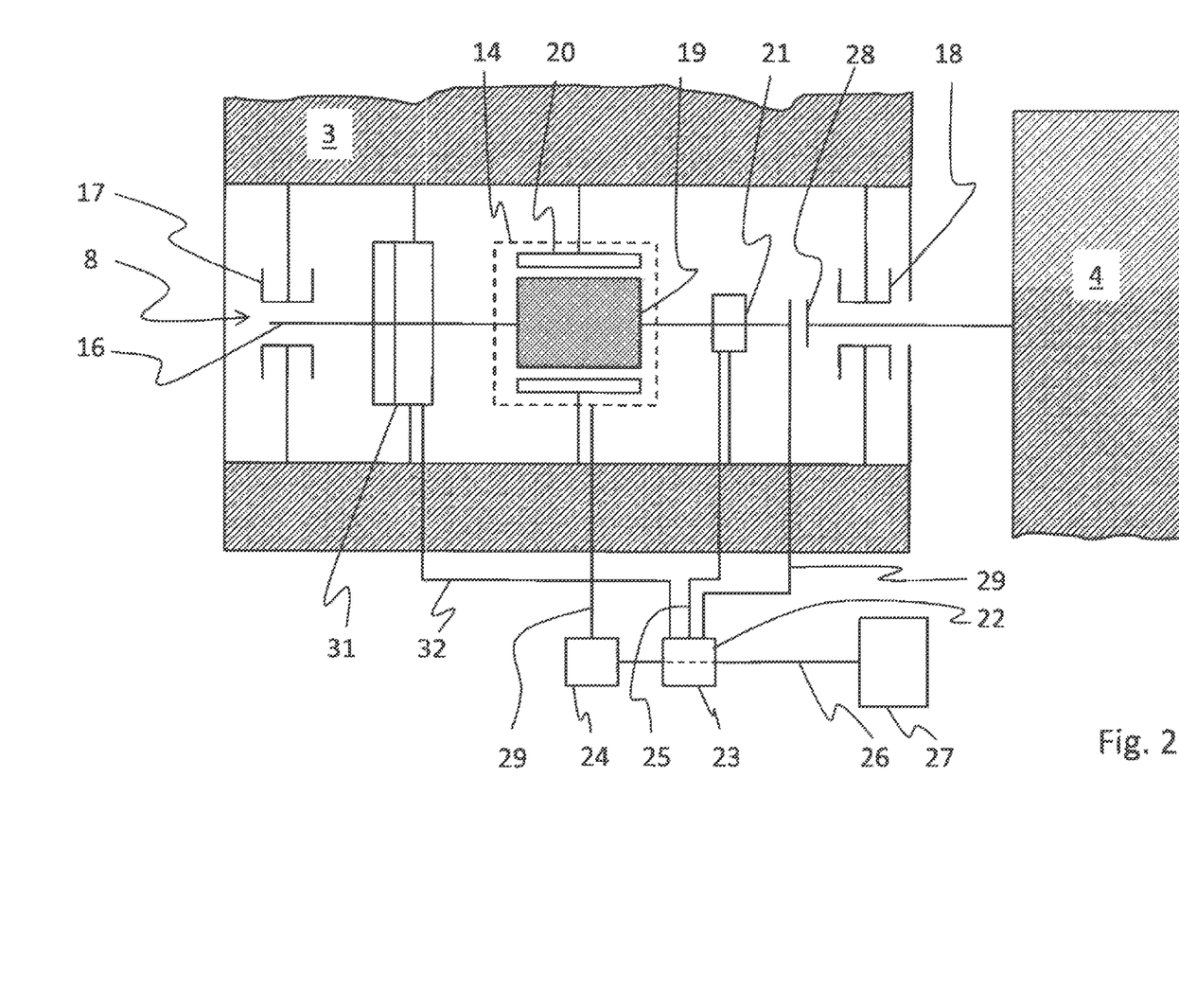
FIG. 2 shows a rotary joint connection of the medical apparatus to an actuator.

Optionally, the medical apparatus, as shown in FIG. 2, can comprise a brake 31, which is arranged between the shaft 16 and the first holding arm 3. The brake 31 is connected to the control unit via a third control line 32. Limit values for forces or moments applied by the actuator or the actuators 14, 15 or for measured forces or moments are stored in a memory of the control unit. If a limit value is exceeded, the brake 31 is activated such that a relative movement between the first holding arm 3 and the second holding arm 4 is at least braked, preferably even suppressed. A safety mechanism is thus provided which reduces the danger of overloading of the actuators 14, 15, of the holding arms 3, 4 or of other parts of the medical apparatus caused, for example, by the influence of unusually strong external forces, wrong operation or control errors.

The brake 31 is preferably dimensioned such that a relative movement between the holding arms 3, 4 can be effectively suppressed even upon application of the maximum torque that can be generated by the first actuator 14.

In the illustrative embodiments, the invention has mainly been described on the basis of the first actuator 14 between the first holding arm 3 and the second holding arm 4. Without restricting the generality of the invention, further actuators can be provided between other holding arms and/or between the front connector rod 6 and the surgical microscope 2, with which further actuators it is possible to generate forces or moments in the direction of one or more of the degrees of freedom of movement predefined by the corresponding joint connection, and which can be controlled via corresponding control units.

The invention is not limited to the illustrated configurations of the holding devices and instead can also be applied to differently constructed holding devices with different numbers of degrees of freedom of movement. Holding devices of a medical apparatus according to the invention can generally comprise both translatory and also rotatory single or multiple joint connections between the holding arms, on which adapted actuators are arranged for generating a longitudinal force and/or a torque. Actuators can be configured electrically, for example, as DC motors, DCBL motors, stepper motors, piezo actuators or traveling wave motors. Alternatively, the actuators used can also be in the form of cylinder drives, membrane drives or so-called "pneumatic muscles". Alternatively or in addition, it is in turn also conceivable to use hydraulic cylinder drives, gear engines, blade engines or piston engines.

The medical apparatus according to the invention and the method for operating it according to the invention are distinguished by the fact that it is possible, on the one hand, to move a medical optical appliance from one position in the work space to another position in the work space by application of a defined force or in a manner almost free of force, and, on the other hand, if necessary, to maintain the medical optical appliance securely and in a controlled manner in a defined position and/or orientation in space. Moreover, equipping the control unit with a position regulator and with a force regulator means that it is possible to dispense with the use of brakes in the operation of the medical apparatus. The use of brakes to fix the medical optical appliance brings a large number of disadvantages. Brakes that are sufficiently dimensioned to be able to retain the holding device securely in different positions in the work space are generally large, heavy and expensive. The brake lining and/or the binding of the brake to the holding device often has a certain flexibility, and the latter promotes vibrations of the stand, which vibrations optionally have to be attenuated by additional dampers. Moreover, when a movement of the holding device is braked using friction brakes, abraded material may develop which can reduce the brake action and can lead to dirtying of the system and, in the worst case, of the operating site. All of these disadvantages can be overcome with the medical apparatus according to the invention.

What is claimed is:

1. Medical apparatus having
a medical optical appliance,
a holding device with at least two holding arms which are connected movably to one another with at least one degree of freedom of movement via a joint, and with an actuator which is connected to the two holding arms in such a way that a force can be exerted via the actuator between the two holding arms in the direction of the degree of freedom of movement, and
a control unit, which comprises a first regulator for outputting a first control signal to the actuator via an adjusting element,
wherein the medical optical appliance is mounted on the holding device,
characterized in that
the control unit comprises means for measuring a kinematic state on the joint and a second regulator for outputting a second control signal to the actuator via the adjusting element,
and the control unit is configured in such a way that it can be set to a first operating state and to a second operating state,
wherein, in the first operating state, the actuator is controlled in a position-regulated manner via the first regulator and the adjusting element as a function of the kinematic state measured on the joint, in such a way that a relative position between the two holding arms is maintained at least substantially independently of external or internal influences on the holding device or the medical optical appliance, and wherein, in the second operating state, the actuator is controlled in a force-regulated manner via the second regulator and the adjusting element, in such a way that a relative movement between the two holding arms is permitted.

2. The medical apparatus according to claim 1, wherein the control unit is configured such that, in the second operating state, it controls the actuator via the second regulator as a function of a kinematic state measured on the joint.

3. The medical apparatus according to claim 1, wherein the control unit comprises means for determining a force generated by the actuator, and in that the control unit is configured in such a way that, in the second operating state, the actuator is controlled via the second regulator as a function of the measured force.

4. The medical apparatus according to claim 3, wherein the medical apparatus has means for blocking a relative movement between the two holding arms, and in that the control unit is configured to cause the relative movement to be blocked when a limit value for the force generated by the actuator is exceeded.

5. Medical apparatus according to claim 1, wherein the medical apparatus comprises an enabling unit which can be activated by a user and which is configured in such a way that an activation of the enabling unit causes a change of the control unit from the first operating state to the second operating state or vice versa.

6. The method for operating a medical apparatus according to claim 1, further comprising:

bringing the control unit to the first operating state, in which a kinematic state on the joint is measured and in which, via the first regulator and the adjusting element, the actuator is controlled in a position-regulated manner as a function of the measured kinematic state, such that a relative position between the two holding arms is at least substantially maintained; and changing the operating state of the control unit to the second operating state, in which the actuator is controlled in a force-regulated manner via the second regulator and the adjusting element, such that a relative movement between the two holding arms is permitted.

7. The method according to claim 6, wherein the change between the operating states is initiated by activation of an enabling unit.

8. The method according claim 6, wherein the first regulator and the second regulator are adapted to each other such that, without the influence of external forces in the second operating state directly after the change, a force exerted by the actuator differs by less than 10% from a force exerted by the actuator in the first operating state directly before the change.

9. The method of claim 6, wherein a force generated by the actuator is measured, and, if a limit value is exceeded, means for blocking a relative movement between the two holding arms are activated, by which means the relative movement is braked and/or suppressed.

* * * * *